(12) United States Patent
Pedersen et al.

(10) Patent No.: US 12,144,494 B2
(45) Date of Patent: Nov. 19, 2024

(54) EMBOLIC PROTECTION VIA BIOLOGIC EFFECT

(71) Applicant: KONINKLIJKE PHILIPS N.V., Eindhoven (NL)

(72) Inventors: John Arthur Pedersen, Eden Prairie, MN (US); Adam Tschida, Greenfield, MN (US); Ben Arcand, Colorado Springs, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 886 days.

(21) Appl. No.: 17/274,455

(22) PCT Filed: Sep. 10, 2019

(86) PCT No.: PCT/EP2019/074042
§ 371 (c)(1),
(2) Date: Mar. 9, 2021

(87) PCT Pub. No.: WO2020/053178
PCT Pub. Date: Mar. 19, 2020

(65) Prior Publication Data
US 2022/0047280 A1 Feb. 17, 2022

Related U.S. Application Data

(60) Provisional application No. 62/729,146, filed on Sep. 10, 2018.

(51) Int. Cl.
*A61B 17/22* (2006.01)
*A61B 17/00* (2006.01)
*A61M 1/00* (2006.01)

(52) U.S. Cl.
CPC ........ *A61B 17/00491* (2013.01); *A61B 17/22* (2013.01); *A61M 1/84* (2021.05);
(Continued)

(58) Field of Classification Search
CPC .. A61M 2025/0004; A61M 2025/1052; A61B 2017/22079; A61B 2017/22081
See application file for complete search history.

(56) References Cited

U.S. PATENT DOCUMENTS

| | | | | |
|---|---|---|---|---|
| 6,022,336 | A | * | 2/2000 | Zadno-Azizi ... A61M 25/10184 604/27 |
| 7,998,162 | B2 | * | 8/2011 | Ho .................... A61M 25/1011 606/194 |

(Continued)

FOREIGN PATENT DOCUMENTS

| | | |
|---|---|---|
| WO | 01/70325 | 9/2001 |
| WO | 2017/062740 | 4/2017 |

OTHER PUBLICATIONS

International Search Report and Written Opinion Dated Nov. 27, 2019 for International Application No. PCT/EP2019/074042 Filed Sep. 10, 2019.

*Primary Examiner* — Laura A Bouchelle (57) ABSTRACT

The present disclosure discussed a device, method and/or system for temporarily closing and/or constricting one or more blood vessels upstream and/or downstream of the vascular intervention site to allow for aspiration of vascular debris resulting from a peripheral vascular surgical procedure so as to effectively remove such debris.

9 Claims, 7 Drawing Sheets

(52) U.S. Cl.
CPC .............. *A61B 2017/00292* (2013.01); *A61B 2017/00778* (2013.01); *A61B 2017/22079* (2013.01)

(56) References Cited

U.S. PATENT DOCUMENTS

| | | |
|---|---|---|
| 2012/0172908 A1 | 7/2012 | Grace |
| 2013/0274673 A1* | 10/2013 | Fischell ............ A61M 25/0084 604/173 |
| 2016/0192912 A1 | 7/2016 | Kassab |

* cited by examiner

EMBOLIC PROTECTION VIA BIOLOGIC EFFECT

CROSS REFERENCE TO RELATED APPLICATIONS

This application is the U.S. National Phase application under 35 U.S.C. § 371 of International Application No. PCT/EP2019/074042 filed Sep. 10, 2019, which claims the benefit of U.S. Provisional Patent Application No. 62/729,146 filed Sep. 10, 2018. These applications are hereby incorporated by reference herein.

FIELD OF THE DISCLOSURE

The present disclosure relates generally to devices, methods and systems associated with intravascular devices and techniques to temporarily close and/or constrict blood vessels for the purpose of capturing embolic debris during an intravascular surgical procedure.

BACKGROUND

Embolic debris is debris, such as plaque that breaks away from a subject's artery or valve, either naturally or during vascular-related procedures. After being dislodged, the embolic debris or smaller particles of the embolic debris can travel from larger arteries through the subject's bloodstream to the smaller arteries in the brain and block them, thereby possibly causing a stroke, which could result in brain damage, or other ischemic damage in tissues other than the brain. Embolic protection devices (EPDs) are used during vascular-related procedures, particularly cardiac-related procedures with elevated embolic risk or peripheral vascular procedures with single-vessel run-off. The use of EPDs reduces the likelihood of complications associated with the potential of debris being released into the bloodstream and possibly causing blockages in smaller blood vessels. EPDs are, therefore, designed to capture the debris that may be dislodged during such procedures.

There are various types of EPDs. One type of EPD is an occlusion device, such as a balloon catheter, which temporarily blocks the flow of blood in a vessel while the vascular interventional procedure is performed. Any embolic debris is trapped in a stagnant column of blood, which can be removed through an aspiration catheter prior to removing the occlusion device. There are both distal occlusion devices and proximal occlusion devices. Distal occlusion devices are located within the subjects vasculature downstream of the surgical intervention site, and proximal occlusion devices are located upstream of the surgical intervention site.

Due to the size of the commercially available EPDs, they are most often used with coronary-related interventional procedures and less commonly used with peripheral-related interventional procedures because the amount of embolic debris from lesions in the peripheral vasculature can be substantially larger than the amount of debris from coronary lesions.

SUMMARY

Accordingly, there is a need for a device, method and/or system for capturing vascular debris resulting from a peripheral vascular surgical procedure so as to effectively remove such captured debris. The present disclosure discusses such a device, method and/or system. An example of a use of an intravascular treatment system in accordance with this disclosure includes temporarily closing and/or constricting one or more blood vessels upstream and/or downstream of the vascular intervention site.

The present disclosure presents a method of treating a subject, wherein the subject comprises a vascular system, the method comprising identifying a target area within the vascular system of the subject, providing a catheter within the vascular system, wherein the catheter comprises a distal portion and a proximal portion; a first lumen comprising a first opening disposed at the distal portion of the catheter, an aspiration lumen comprising a second opening disposed at the distal portion of the catheter, providing an introducer within the first lumen of the catheter, wherein the introducer comprises a needle having an exit port, wherein the introducer is slidable relative to the introducer, inserting the needle into the target area and introducing a pharmacological agent to the target area via the exit port, wherein the pharmacological agent initiates a temporary vasospasm at the target area, performing a vascular interventional technique, and aspirating debris resulting from the vascular interventional technique through the aspiration lumen.

The method according to the previous paragraph further comprising the step of aspirating fluid from the target area to facilitate the temporary vasospasm.

The method according to any of the previous paragraphs, wherein the step of performing a vascular interventional technique occurs upstream of the target area.

The method according to any of the previous paragraphs, wherein the step of performing a vascular interventional technique occurs downstream of the target area.

The method according to any of the previous paragraphs, wherein the vascular system comprises a peripheral vascular system, and the target area is within the peripheral vascular system.

The method according to any of the previous paragraphs, wherein the vascular system comprises a coronary vascular system, and the target area is within the coronary vascular system.

The method according to any of the previous paragraphs, wherein the second opening is at a distal end of the distal portion of the catheter.

The method according to any of the previous paragraphs, wherein the second opening is at location proximal a distal end of the distal portion of the catheter.

The method according to any of the previous paragraphs, wherein the second opening is in or through a wall of the catheter.

The present disclosure also presents a method of treating a subject, wherein the subject comprises a vascular system, the method comprising identifying a target area within the vascular system of the subject, providing a catheter within the vascular system, wherein the catheter comprises a distal portion and a proximal portion, a first lumen comprising a first opening disposed at the distal portion of the catheter, an aspiration lumen comprising a second opening disposed at the distal portion of the catheter, providing an introducer within the first lumen of the catheter, wherein the introducer comprises a distal portion having a releasable carrier, wherein the carrier includes an adhesive, wherein the introducer is slidable relative to the introducer, delivering the carrier to the target area and introducing the adhesive to the target area, performing a vascular interventional technique, and aspirating debris resulting from the vascular interventional technique through the aspiration lumen.

The method according to the previous paragraph further comprising the step of aspirating fluid from the target area to facilitate closure of the vascular system at the target area.

The method according to any of the previous paragraphs, wherein the step of performing a vascular interventional technique occurs upstream of the target area.

The method according to any of the previous paragraphs, wherein the step of performing a vascular interventional technique occurs downstream of the target area.

The method according to any of the previous paragraphs, wherein the vascular system comprises a peripheral vascular system, and the target area is within the peripheral vascular system.

The method according to any of the previous paragraphs, wherein the vascular system comprises a coronary vascular system, and the target area is within the coronary vascular system.

The present disclosure also presents an intravascular treatment system comprising a catheter comprising a distal portion and a proximal portion, and a first lumen comprising a first opening disposed at the distal portion of the catheter, and a second lumen comprising a second opening disposed at the distal portion of the catheter, wherein the second lumen comprises a proximal opening, wherein the proximal opening is capable of being coupled to an aspiration system, and an introducer slidably disposed within the lumen of the catheter, wherein the introducer comprises a distal portion, wherein the distal portion comprises a carrier having an adhesive.

The system according to the previous paragraph, wherein the introducer comprises a means for releasing the carrier.

The system according to any of the previous paragraphs, wherein the means for releasing the carrier is capable of recapturing the carrier.

The system according to any of the previous paragraphs, wherein the second opening is at a distal end of the distal portion of the catheter.

The system according to any of the previous paragraphs, wherein the second opening is at location proximal a distal end of the distal portion of the catheter and wherein the second opening is in or through a wall of the catheter.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

The term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
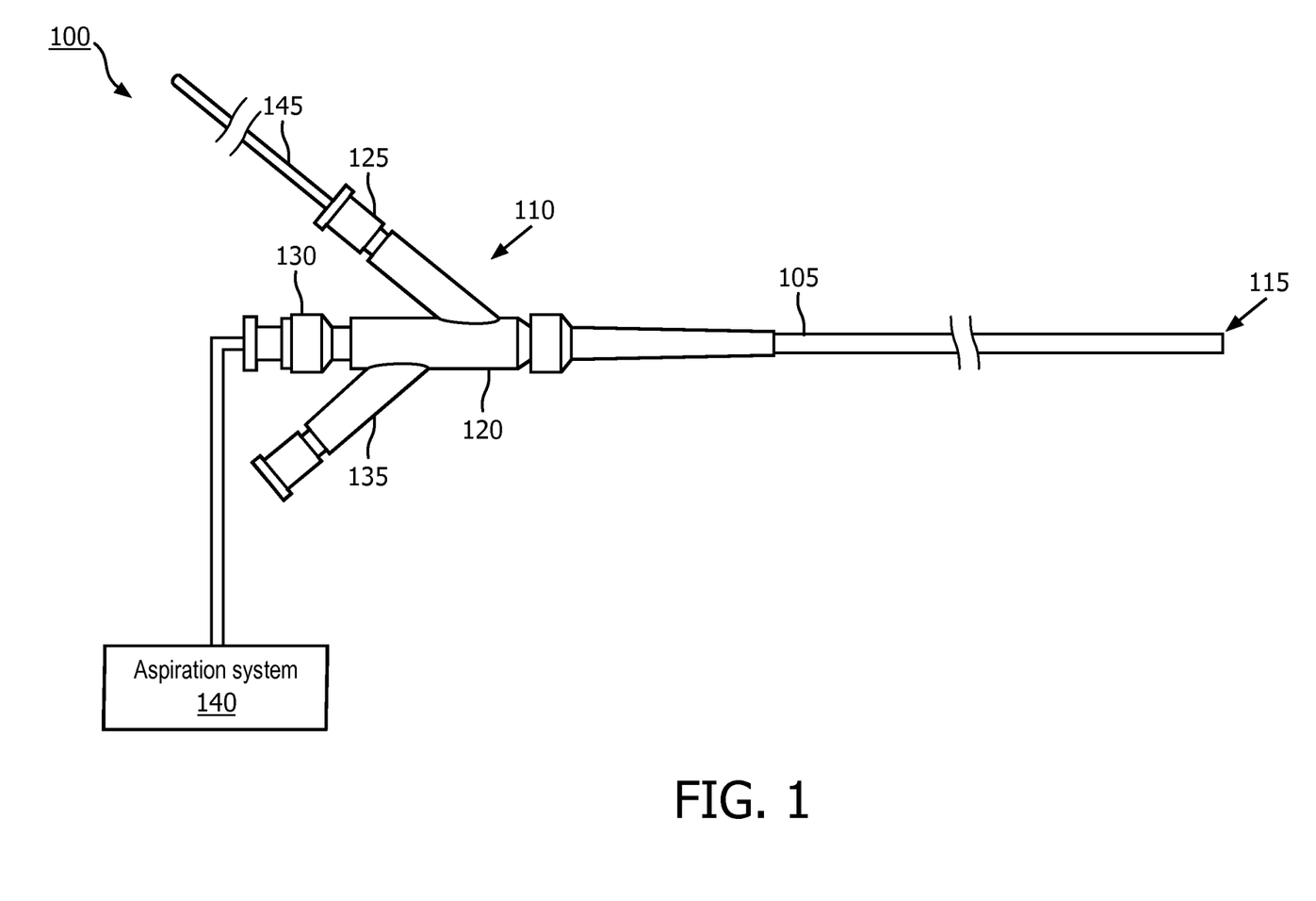
FIG. 1 shows a vascular treatment system according to the present disclosure.

The present disclosure relates generally to devices, methods and systems associated with intravascular devices and techniques to temporarily close and/or constrict blood vessels for the purpose of capturing embolic debris created during an intravascular surgical procedure. Referring to FIG. 1, there is shown an exemplary vascular treatment system 100 used to temporarily close and/or constrict blood vessels for the purpose of capturing embolic debris. The system 100 illustrated in FIG. 1 includes a catheter 110 and an aspiration system 140. The catheter 110 includes a distal portion 115, an intermediate shaft portion 105, and a proximal portion 120. The proximal portion 120 may include one or more (e.g., two, three, four, etc.) adapters 125, 130, 135 into which other surgical instruments are introduced and/or coupled to. If the adapters are integrated into the proximal portion 120 of the catheter 110, the proximal portion may be referred to as a bifurcate, trifurcate, etc. and serve as a handle for the catheter 110.

FIG. 1 shows a catheter 110 with an elongated body having an over the wire (OTW) design. The OTW design includes a guidewire lumen (not shown) into which a guidewire (not shown) may be inserted. For example, each of the adapters 125, 130, 135 may be fluidly coupled to separate and corresponding lumens 160, 165, 155 (FIG. 2) that extend from the proximal portion 120 of the catheter 110 to the distal portion 115. Alternatively, the adapters 125, 130, 135 may be fluidly coupled to one or more common lumens 160, 165, 155 extending from the proximal portion 120 of the catheter 110 to the distal portion 115.

A guidewire may be inserted into the any of the adapters 125, 130, 135. FIG. 1 depicts an introducer 145 inserted in a first adapter 125 and the aspiration system 140 being coupled to the second adapter 130. FIG. 1 does not depict anything coupled to a third adapter 135. So, the guidewire may be inserted into the third adapter 135. Otherwise, the guidewire may be inserted into and removed from either the first adapter 125 or the second adapter 130 prior to the coupling of and/or introduction of the introducer 145 into the first adapter 125 and/or by the aspiration system 140 into the second adapter 130. Although FIG. 1 depicts an OTW design, the catheter may include a rapid exchange (RX) design, which typically includes an adapter coupled to the longitudinal portion of the catheter in a position distal of the proximal portion 120.

The intravascular catheter 110 is configured for intraluminal introduction to a target body lumen. The dimensions and other physical characteristics of the catheter bodies will vary significantly depending on the body lumen that is to be accessed. Catheter bodies intended for intravascular introduction will typically have a length in the range from 50 cm to 200 cm and an outer diameter in the range from 1 French to 12 French (0.33 mm:1 French), usually from 3 French to 9 French. Catheter bodies will typically be composed of an organic polymer that is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase qualities such as rotational strength, column strength, toughness, or pushability. Suitable catheter bodies may be formed by extrusion, with one or more channels being provided when desired. The catheter diameter can be modified by heat expansion and shrinkage using conventional techniques. The resulting catheters will thus be suitable for introduction into the vascular system, often the coronary arteries, by conventional techniques.

As noted, in certain aspects, the catheter body may be reinforced for torsional rigidity to increase axial torque transmission from the proximal to distal portion of the body. Torsional rigidity may be augmented through a variety of torsion members including wires, spines, shafts, braided or coiled materials, or a combination thereof. These members may be disposed around, on, or within some portion of the catheter body. Various members for increasing torsional rigidity are presented. An axial torque transmitting shaft may be an extruded single lumen, an extruded dual lumen, or an extruded single lumen with two shafts running through it. These lumens may be free floating or fixed between the proximal and distal ends of the catheter body but, in most embodiments, should be fixed to one or more of the guidewire lumens at the distal portion of the body. Fixation may be through heat fusion, adhesive, or other means known in the art. In certain embodiments, the axial torque transferring mechanism may include a separate lumen with a shaft run therethrough.

In certain aspects, the catheter may include a shaft made of a braided or coiled material, where the braided or coiled material is terminated at the distal and proximal ends in circumferential bands. The shaft may be terminated by coupling the cut braids at both proximal and distal ends with small bands or reducing the pitch of a coil at both ends until the coils are substantially touching. The shaft may be coupled to one or both of the guidewire lumens or otherwise joined to the catheter body at least at the distal portion. A torsion shaft may be incorporated in the construction of the catheter. In certain aspects, the inner diameter of the catheter body may be lined with a polymeric liner and the entire assembly may be reflowed to integrate the shaft into the catheter body. In some embodiments, the small bands coupling the cut braids at the distal and proximal ends of the shaft may be constructed of a polymer and can provide a surface which is easier to bond to the catheter body during manufacturing. To aid in visualization and orientation of the distal portion of the body and the exit ports within vasculature, the distal portion of the body may include a pattern of radiopaque or other markers which may be externally monitored via, for example, x-ray.

In certain embodiments, catheters of the present disclosure may include one or more centering mechanisms disposed on the catheter body, catheter tip, or the imaging apparatus support. Centering mechanisms may be disposed at any suitable location along the length of the catheter body. In preferred embodiments, centering mechanisms are disposed near the distal end of the catheter and/or the first and/or second exit ports so that the first and/or second exit ports may be centered within a vessel by the centering mechanism. Centering mechanisms may include, for example, inflatable balloons, or collapsible structures such as a sheathable nitinol basket or other structure comprising a shape memory material. Centering mechanisms may have an unexpanded state in which they remain close to the catheter body and an expanded state wherein the centering mechanism expands radially from the surface of the catheter body in order to interact with a lumen wall to center the first and/or second exit ports within a cross-section of a vessel, artery, or other body lumen. A balloon centering mechanism may transition between an unexpanded and expanded state through application of a fluid or gas to inflate the one or more balloons. The catheter body may include an air or fluid line connecting the balloon centering mechanism to an air or fluid source. A pump may be used to force air or fluid into the centering balloon in order to expand it. Balloon centering mechanisms may be of any suitable shape or size.

Figure 2:
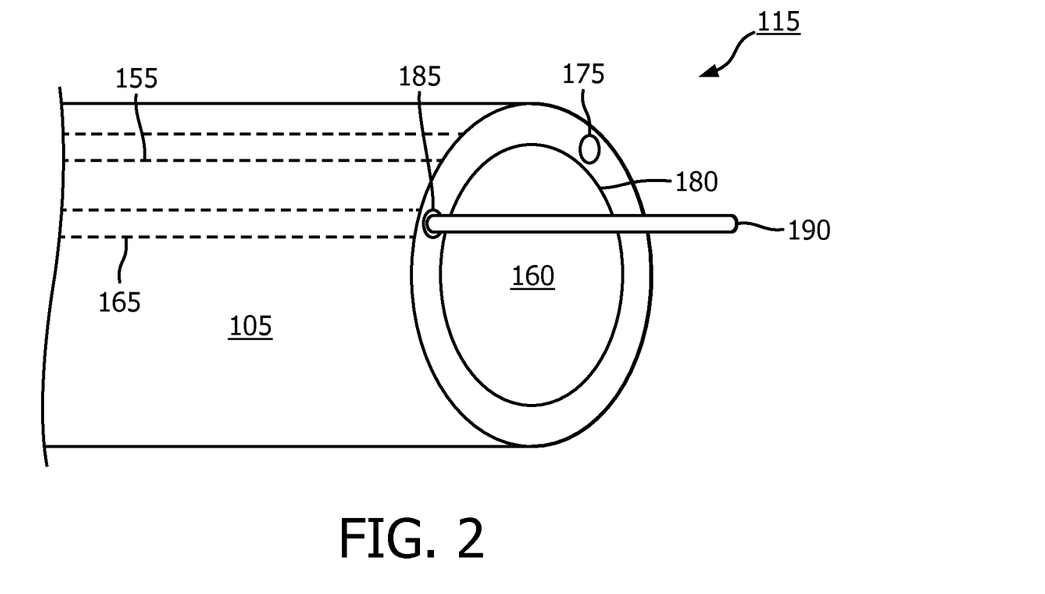
FIG. 2 shows an elevation view of the distal portion of an aspiration catheter.

Referring to FIG. 2, there is shown an enlarged elevation view of the distal portion 115 of the catheter 110, particularly the distal end of the catheter shaft 105. As discussed above, the catheter 110 may include multiple lumens 155, 160, 165 extending from the proximal portion 120 of the catheter 110 to the distal portion 115. For example, assuming each of the first, second and third adapters 125, 130, 135 is fluidly coupled to separate lumens, the catheter 110 will include a first lumen 175, a second lumen 180, and a third lumen 185, and the distal portion 115 of the catheter 110 will include corresponding first, second and third openings 175, 180, 185 fluidly coupled to the first lumen 155, second lumen 160, and third lumen 165, respectively.

Figure 3:
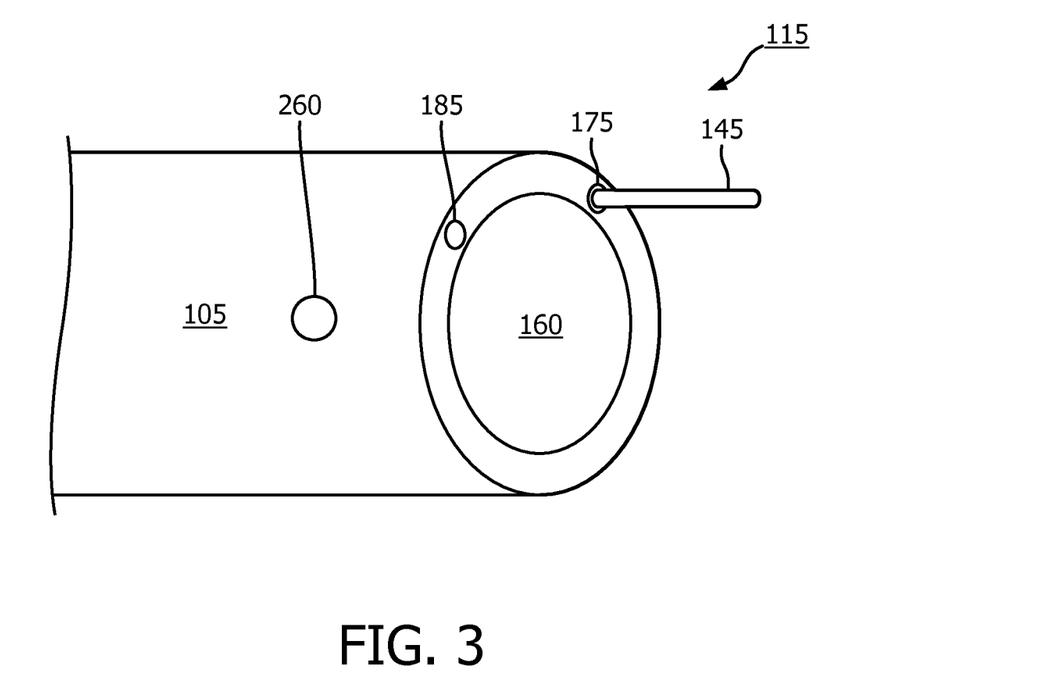
FIG. 3 shows an elevation view of the distal portion of the aspiration catheter with an introducer extending therefrom.

Assuming that the introducer 145 is introduced into the first adapter 125 and through the first lumen 175, the introducer 145 will be capable of slidably moving relative to the catheter shaft 105 and extending from the first opening 175. And, in this example, the first adapter 125, the first lumen 155 and the first opening 175 may be referred to as the introducer adapter 125, the introducer lumen 155 and the introducer opening 175. Assuming that the aspiration system 140 is fluidly coupled to the second adapter 130, the second lumen 160, and the second opening 180, these items may be referred to as the aspiration adapter 130, the aspiration lumen 160, and the aspiration opening 180. Assuming that the guidewire 190 is introduced into the third adapter 135 and through the third lumen 165, the guidewire 190 will be capable of slidably moving relative to the catheter shaft 105 and extending from the third opening 185. And, in this example, the third adapter 135, the third lumen 165 and the third opening 185 may be referred to as the guidewire adapter 135, the guidewire lumen 165 and the guidewire opening 185. Referring to FIG. 3, the catheter shaft 105 may also include an aspiration opening 260 that is disposed on the side of the catheter shaft and proximally of the distal end of the catheter shaft. The aspiration opening 260 may be constructed to be only in the outer (side) wall of the catheter shaft and fluidly coupled to a separate aspiration lumen within the catheter shaft wall, wherein the separate aspiration lumen is fluidly coupled to separate aspiration system (not shown) via an additional aspiration port (not shown). Or the aspiration opening 260 may be constructed to be through the side wall of the catheter shaft such that the aspiration lumen 260 is fluidly coupled to the aspiration system 140 and the second adapter 130.

Referring again to FIG. 1, the aspiration system 140 may comprise a means for creating a pressure differential within the system itself, a lumen in the catheter 110 and the vasculature. The pressure differential may be constant pressure, variable pressure, alternating pressure such as a series of pulses, and/or a combination thereof. The means for creating a pressure differential may include a pump, such as a vacuum pump or a peristaltic pump. If a vacuum pump is used, the vacuum pump may be connected to a pulse width modulator, which may be in operative communication with a solenoid valve, the actuation of which creates one or more pressure differentials to the aspiration system. Accordingly, rather than creating a constant pressure differential (e.g., suction) within a lumen of the catheter 110, the aspiration system 140 of the present disclosure may apply alternative pressure(s), thereby creating pulses of suction pressure within the lumen.

Figure 10:
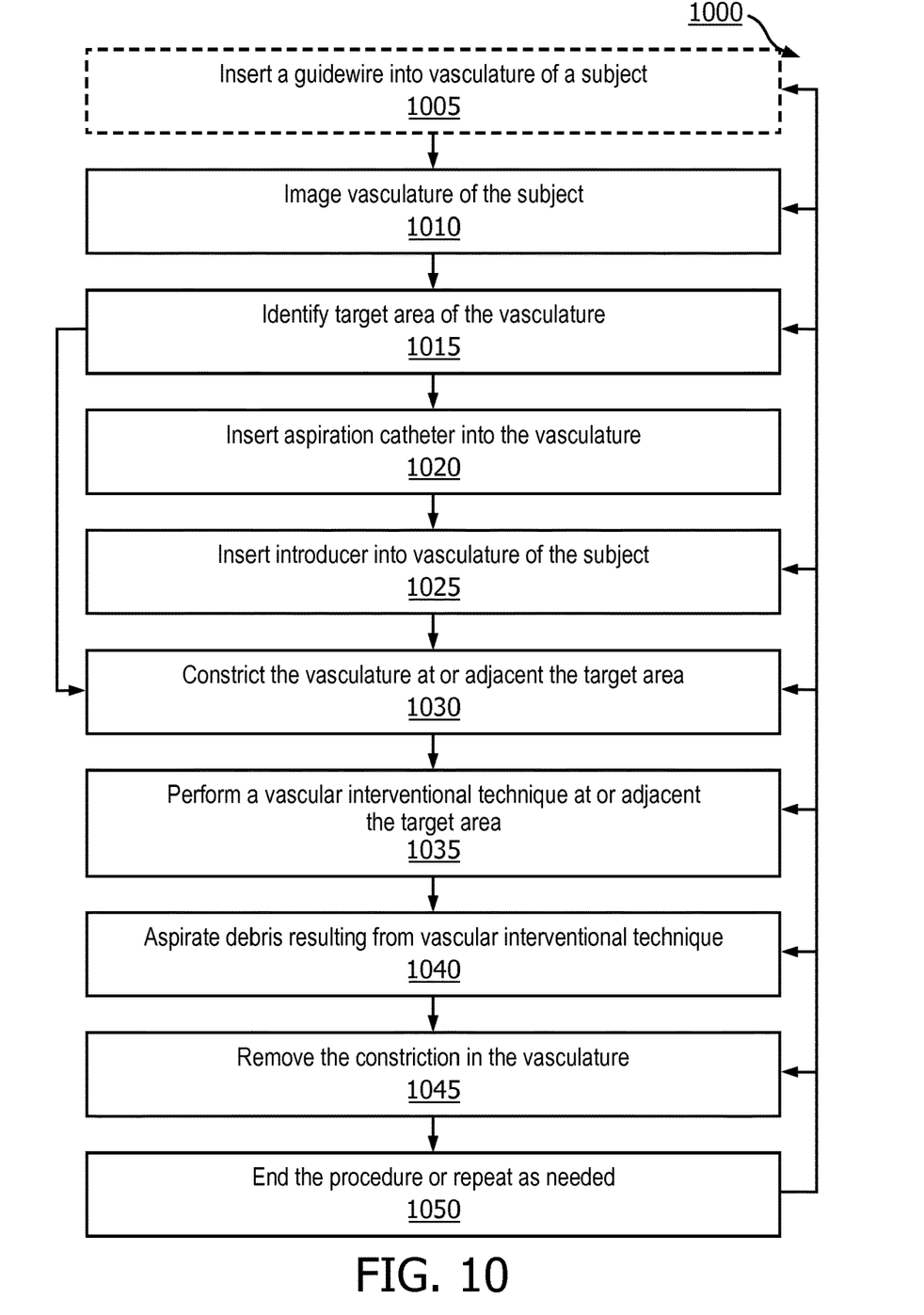
FIG. 10 shows a block diagram or flow chart of operating and/or using the vascular treatment system and the device(s) discussed herein.

Referring to FIG. 10, there is shown a block diagram or flow chart of operating and/or using the vascular treatment system 100 of FIG. 1. The method 1000 of operating and/or using the vascular treatment system 100 may include one or more of the following steps, indicated as items 1005, 1010, 1015, 1020, 1025, 1030, 1035, 1040, 1045 and 1050. Step 1005 includes inserting a guidewire into the vasculature of a subject. Step 1010 imaging the vasculature of the subject. Step 1015 includes identifying a target area of the vasculature. Step 1020 includes inserting an aspiration catheter into the vasculature. Step 1025 includes inserting an introducer into the vasculature of the subject. Step 1030 includes constricting the vasculature at or adjacent the target area, including using the introducer to facilitate the creation of the constriction. Step 1035 includes performing a vascular interventional technique at or adjacent the target area. Step 1040 includes aspirating debris resulting from the vascular interventional technique. Step 1045 includes removing the constriction in the vasculature after performing the interventional technique. Step 1050 includes ending the procedure or repeating the procedure, or any portion or portions thereof.

Step 1005, which includes inserting a guidewire 190 into the vasculature of a subject, is an optional step. It may be desirable to insert the guidewire 190 into the vasculature prior to introducing the catheter 110 in order to more easily insert the catheter 110 into the vasculature by sliding the catheter 110 over the guidewire 190. For example, FIG. 2, which is discussed above, illustrates the guidewire 190 disposed within the third lumen 165 and extending through and from opening 185 at the distal portion 115 of the catheter shaft 105 within the vasculature.

The step of inserting the guidewire 190 into the vasculature of the subject may be used prior to, in conjunction with (e.g., simultaneously with) and/or subsequent to step 1010, which includes imaging the vasculature of the subject. Various types of imaging devices and techniques, such as ultrasound devices, magnetic imaging devices, fluoroscopy, etc., may be used to perform this step.

Step 1015, which includes identifying a target area of the vasculature, as well as the other or remaining steps in method 1000, may also be performed using the imaging devices and techniques. As such, after the target area in the vasculature is identified, an aspiration catheter 110 is inserted into the vasculature at and/or adjacent the target area as set forth in step 1020. At this point in the procedure, the guidewire 190 may be removed or remain in the catheter 110 and vasculature.

Assuming the guidewire 190 is removed after the catheter 110 inserted, FIG. 3 illustrates the introducer 145, particularly the distal portion of the introducer 145, extending from the opening 175 in distal portion 115 of shaft 105 of the aspiration catheter 110, after the introducer 145 has been inserted into the vasculature of the subject the lumen 155. At this point of the method 1000, the aspiration catheter 110 may be used to constrict the vasculature of the subject, as set forth in step 1020.

Figure 4A:
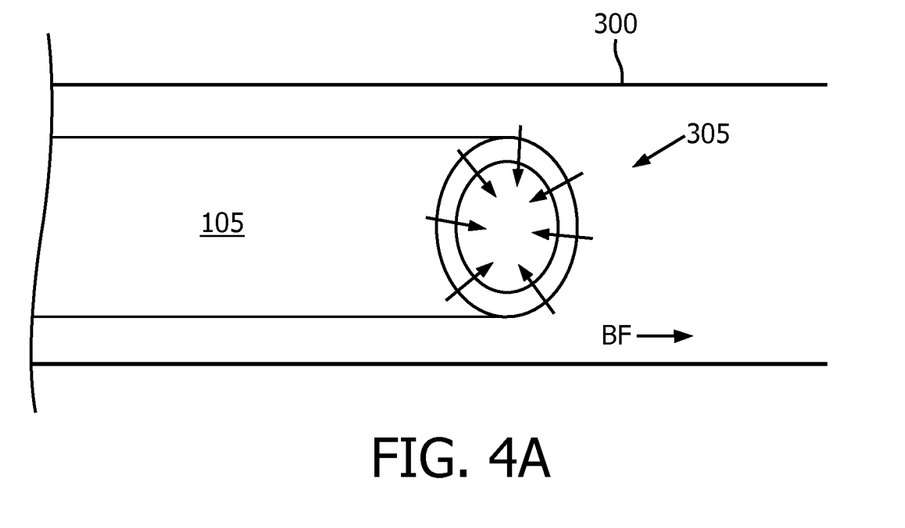
FIG. 4A shows an elevation view of the distal portion of the aspiration catheter within the vasculature of a subject.
Figure 4B:
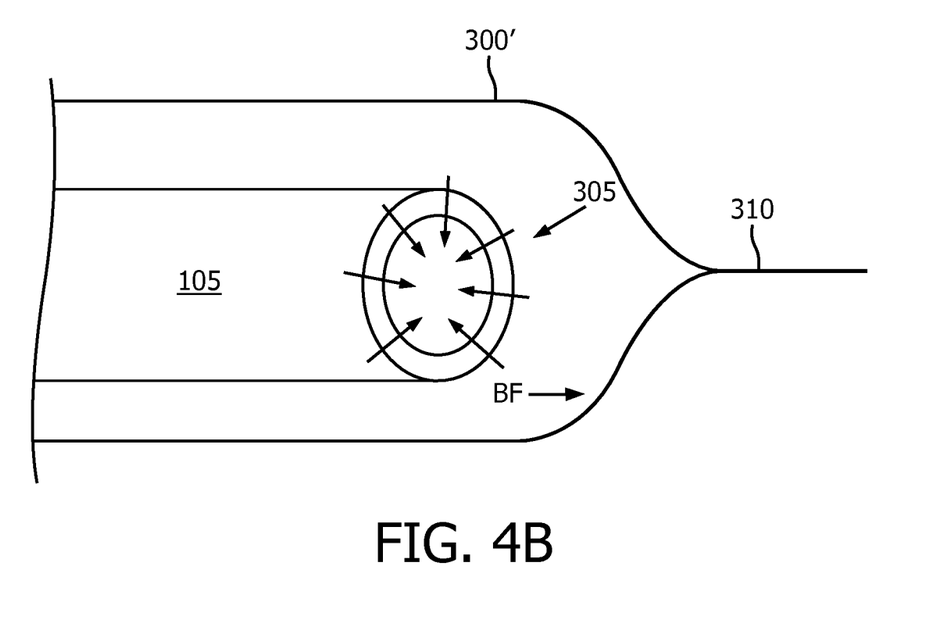
FIG. 4B shows an elevation view of the distal portion of the aspiration catheter within the vasculature of a subject adjacent a constriction in the vasculature.

Referring to FIG. 4A, the catheter shaft 105 depicted as being inserted and/or disposed in the vasculature 300 such that the catheter's aspiration opening 180 is facing the same direction in which the intravascular fluid (e.g., blood) is flowing. The direction of the intravascular fluid flow is indicated as item "BF." Once the catheter shaft 105 is at and/or adjacent the target area within the vasculature 300, as depicted in FIG. 4A, the aspiration system 140 may be turned "ON," and upon doing so, intravascular fluid is drawn into the catheter's aspiration opening 180, through the aspiration lumen 160 (and/or the aspiration opening 260) and to the aspiration system 140 via the aspiration port 130 (and/or a separate aspiration lumen, aspiration system via an additional aspiration port—all of which may be fluidly coupled to the aspiration opening 260). The movement or drawing of the intravascular fluid into the catheter's aspiration opening 180 is depicted in FIG. 4A as arrows 305. Aspiration may not only draw intravascular fluid into the catheter's aspiration opening 180, but doing so, may also collapse and close (either partially or fully) the vasculature 300', thereby creating a constriction 310 therein, as shown in FIG. 4B.

Figure 5A:
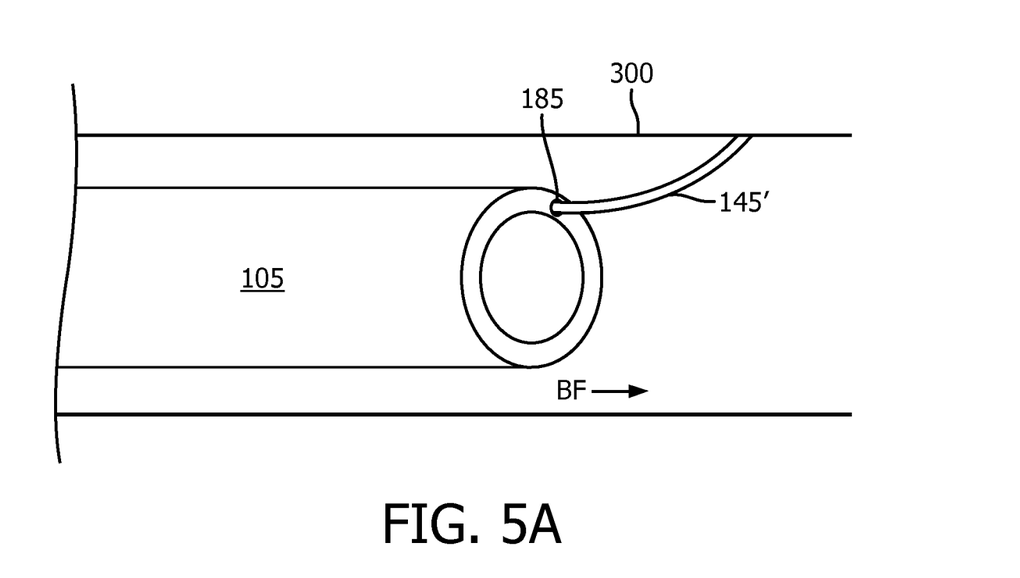
FIG. 5A shows an elevation view of the distal portion of the aspiration catheter within the vasculature of a subject with an introducer extending therefrom, wherein the introducer includes a needle that is inserted into the vasculature.

In an effort to further facilitate constriction of the vasculature 300', an introducer 145 may be inserted into the vasculature 300, such as into the catheter 110, particularly into the introducer adapter 125, through the introducer lumen 155 and extending from the introducer opening 175 as depicted in FIG. 3. Referring to FIG. 5A, the introducer 145' may include a needle capable of injecting a pharmacological agent into the vasculature 300 to initiate a temporary vasospasm, which leads to a vasoconstriction. Examples of such pharmacological agents include—without limitation stimulants (amphetamine, caffeine, cocaine, methylphenidate, pseudoephedrine), andrenergic agonists (adrendaline, epinephrine, isoprenaline, metaraminol, noradrenaline, norepinephrine, oxymetazoline, phenylephrine,), as well as hormones and their analogs (angiotensin II, antidiuretic hormone (ADH), felypressin). After the agent is injected into the vasculature 300, the needle 145' may be retracted either partially or fully into the introducer lumen 155, thereby allowing the vasculature 300' to collapse and close (either partially or completely) during aspiration to create a constriction 310 therein, as shown in FIG. 4B.

Figure 6A:
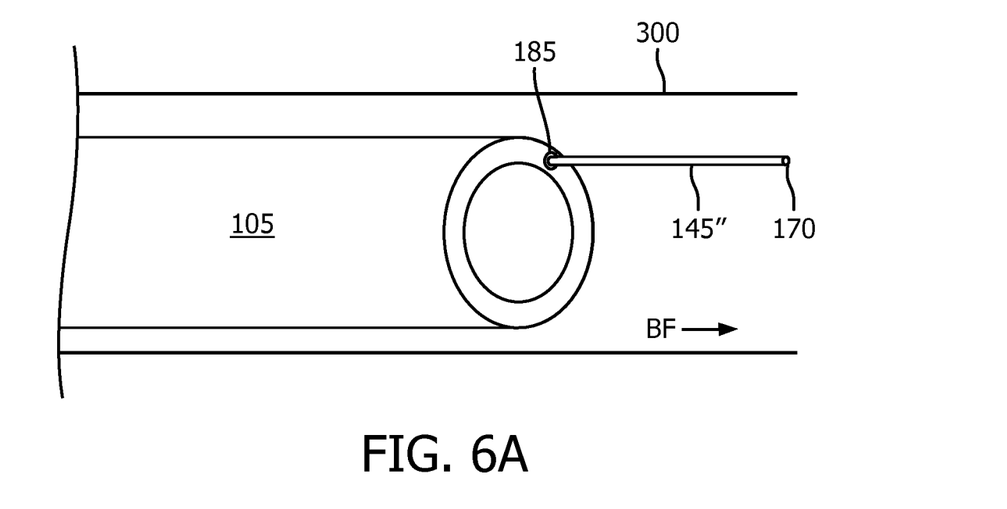
FIG. 6A shows an elevation view of the distal portion of the aspiration catheter within the vasculature of a subject with an introducer extending therefrom, wherein the introducer includes an adhesive.
Figure 6B:
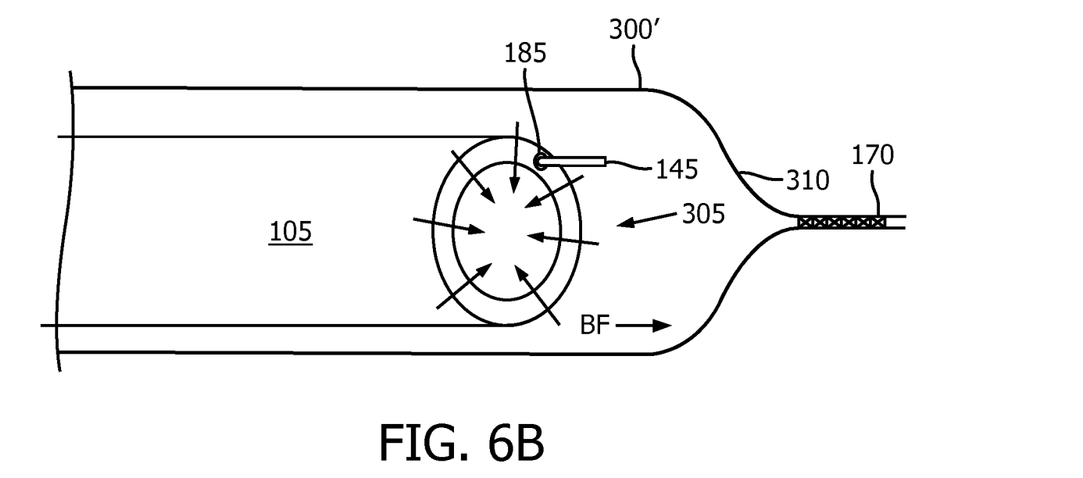
FIG. 6B shows an elevation view of the distal portion of the aspiration catheter illustrated in FIG. 6A within the vasculature of a subject adjacent a constriction in the vasculature.

In an alternative and/or additional effort to further facilitate constriction of the vasculature 300', the introducer 145 may be include a carrier 170 that includes an adhesive, as depicted in FIG. 6A. The carrier 170 may be releasable from the introducer 145. Accordingly, the introducer may include one or more means for releasing and/or recapturing the carrier 170, such as graspers. Examples of such adhesives may include cyanoacrylates, polysaccharide-based hydrogel formed by reacting oxidized dextran and chitosan, hydrogel tissue adhesives formed by reacting an oxidized polysaccharide with a water-dispersible multi-arm polyether amine, fibrin-based adhesives, and mussel adhesive proteins (containing a high concentration of the catecholic amino acid dihydroxyphenylalanine (DOPA)).

Figure 5B:
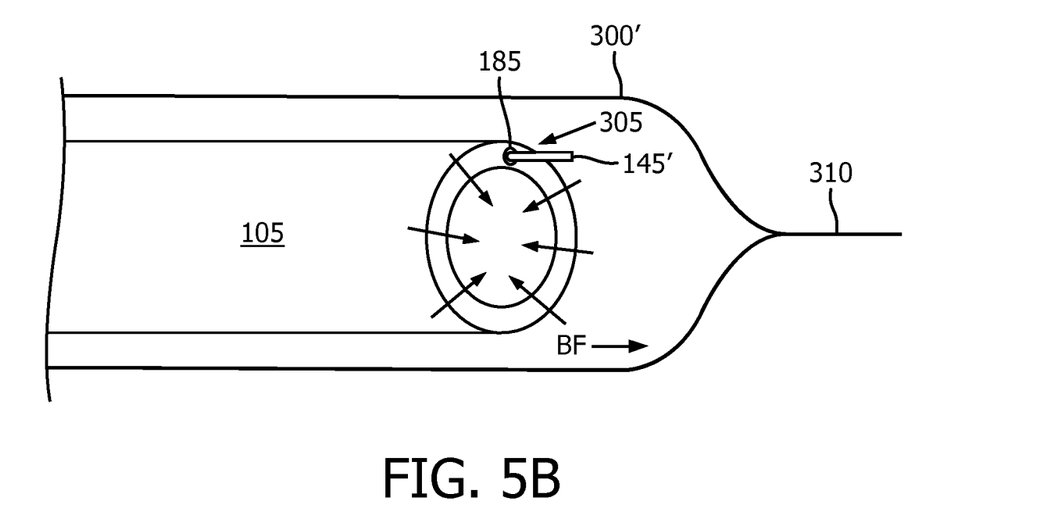
FIG. 5B shows an elevation view of the distal portion of the aspiration catheter illustrated in FIG. 5A within the vasculature of a subject adjacent a constriction in the vasculature.

After the carrier 170 and adhesive is disposed at and/or adjacent the target area of the vasculature 300, aspiration is initiated, and the vasculature 300' collapses and/or closes (either partially or fully) upon the carrier and/or the adhesive to create a constriction 310 therein, as shown in FIG. 5B. The carrier 170 and/or the adhesive may increase the likelihood that the constriction 310 will remain as such during the surgical procedure. After the surgical procedure is completed, the carrier 170 and/or the adhesive may be removed, thereby eliminating the constriction 310 and reopening the vasculature 300.

Figure 7:
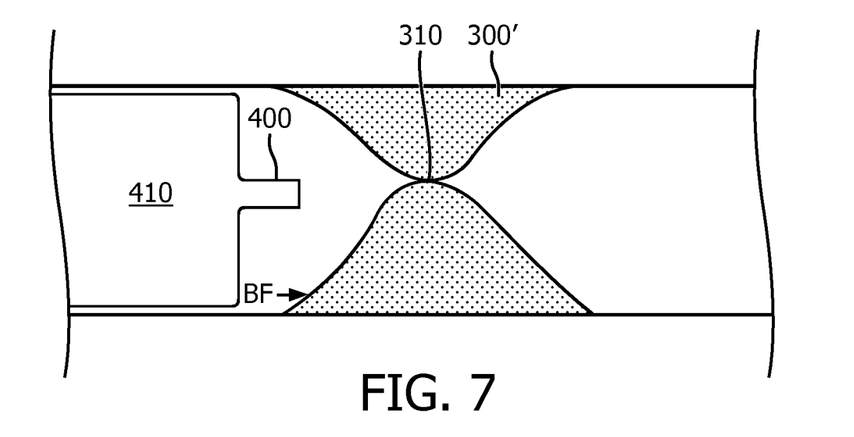
FIG. 7 shows an elevation view of the aspiration catheter upstream of the constriction in the vasculature.

Referring again to FIG. 10, after the constriction 310 has been created within the vasculature 300', a clinician may perform a vascular interventional technique at or adjacent the target area as set forth in step 1035. The vascular interventional technique may be performed either upstream or downstream of the constriction 310. One example of a surgical technique includes angioplasty, such as balloon angioplasty. Referring to FIG. 7, there is shown a balloon catheter 400 upstream of the constriction 310 in the vasculature 300'. During angioplasty, a deflated balloon 410, which is attached to a catheter 400 is disposed at and/or adjacent the target area. The balloon 410 is subsequently inflated, thereby forcing expansion of the vasculature and the surrounding muscular. A stent may also be inserted during the procedure to ensure the target area remains open. The balloon 410 is deflated and subsequently withdrawn, and the vascular interventional technique is completed.

Figure 8:
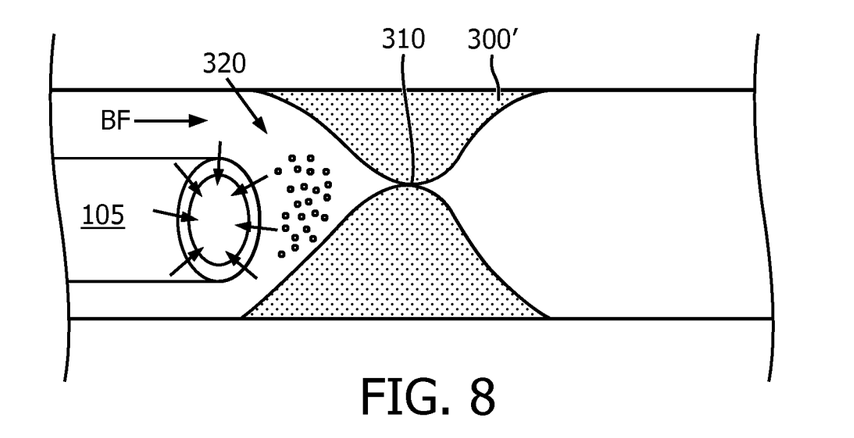
FIG. 8 shows an elevation view of balloon catheter upstream of the constriction in the vasculature.

During performance of the vascular interventional technique, it is possible that debris 320 may have become disclosed from the vasculature 300. Therefore, after completion of the vascular interventional technique, it may be desirable to aspirate the vasculature and remove the debris as set forth in step 1040 in FIG. 10. FIG. 8 depicts the distal portion of the shaft 105 and aspiration opening of the catheter 110 upstream of the constriction 310 at and/or adjacent the target area in the vasculature, aspirating and removing debris 320 therefrom.

After the debris is aspirated, the catheter 115 is removed from the vasculature, and the constriction 310 can be removed. Alternatively, before or after the constriction is removed, any portion of the procedure may be repeated, as shown in step 1050 in FIG. 10. The constriction may be removed by injecting the target area in the vasculature with a different pharmacological agent to reverse the vasospasm and/or removing the carrier and adhesive.

The method described above, discussed the aspiration catheter and the surgical technique being introduced on the same side of the constriction and the aspiration catheter entering the vasculature in the same direction as the intravascular fluid (BF) is flowing. As such, the surgical procedure is performed upstream of the constriction. However, the aspiration catheter and the surgical technique can be introduced on the same side of the constriction entering the vasculature but in the opposite direction as the intravascular fluid (BF) is flowing. As such, the surgical procedure is performed downstream of the constriction.

Figure 9:
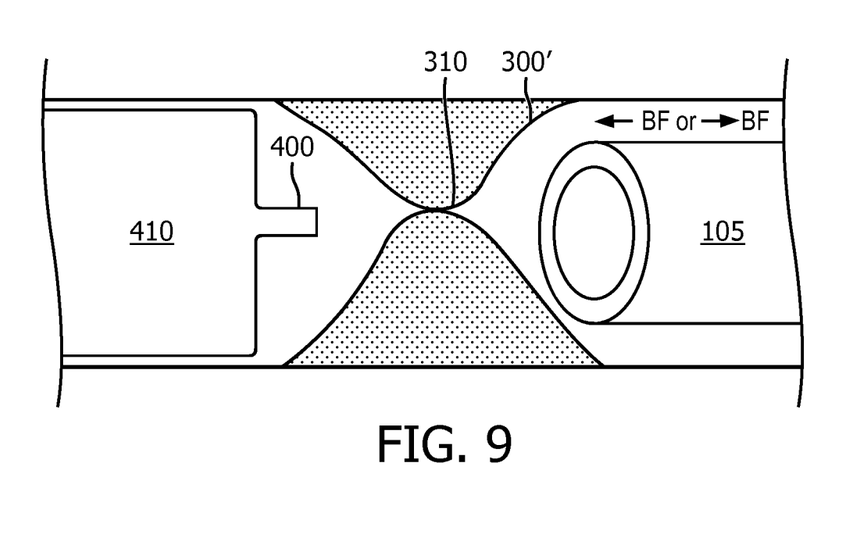
FIG. 9 shows a. shows an elevation view of the aspiration catheter on one side of the constriction in the vasculature and a balloon catheter on the other side of the constriction.

Furthermore, the aspiration catheter and the surgical instrument, such as the balloon catheter, used to perform the technique can be introduced on opposite sides of the constriction, as depicted in FIG. 9. And either the aspiration catheter or the surgical instrument can enter the vasculature in the same and/or opposite direction as the intravascular fluid (BF) is flowing. That is, the aspiration catheter may be introduced from one direction in the vasculature, and the surgical instrument may be introduced from the opposite direction in the vasculature, regardless of the direction in which the intravascular fluid (BF) is flowing. In such case, the aspiration catheter may create the constriction, and the surgical instrument may be used on the other side of the constriction. In this configuration, the aspiration catheter may be used before, during and/or after introduction of the surgical instrument and use thereof to perform the surgical technique, and the aspiration catheter and surgical instrument may be used either simultaneously or serially.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of treating a subject, wherein the subject comprises a vascular system, the method comprising:
   identifying a target area within the vascular system of the subject;
   providing a catheter within the vascular system, wherein the catheter comprises:
   a distal portion and a proximal portion;
   a first lumen comprising a first opening disposed at the distal portion of the catheter;
   an aspiration lumen comprising a second opening disposed at the distal portion of the catheter;
   providing an introducer within the first lumen of the catheter, wherein the introducer comprises a needle having an exit port, wherein the introducer is slidable relative to the first lumen of the catheter;
   inserting the needle into the target area and introducing a pharmacological agent to the target area via the exit port, wherein the pharmacological agent initiates a temporary vasospasm at the target area;
   performing a vascular interventional technique; and
   aspirating debris resulting from the vascular interventional technique through the aspiration lumen.

2. The method of claim 1 further comprising the step of aspirating fluid from the target area to facilitate the temporary vasospasm.

3. The method of claim 1, wherein the step of performing a vascular interventional technique occurs upstream of the target area.

4. The method of claim 1, wherein the step of performing a vascular interventional technique occurs downstream of the target area.

5. The method of claim 1, wherein the vascular system comprises a peripheral vascular system, and the target area is within the peripheral vascular system.

6. The method of claim 1, wherein the vascular system comprises a coronary vascular system, and the target area is within the coronary vascular system.

7. The method of claim 1, wherein the second opening is at a distal end of the distal portion of the catheter.

8. The method of claim 1, wherein the second opening is at location proximal a distal end of the distal portion of the catheter.

9. The method of claim 8, wherein the second opening is in or through a wall of the catheter.

* * * * *